United States Patent [19]
Neuenschwander et al.

[11] Patent Number: 5,665,831
[45] Date of Patent: Sep. 9, 1997

[54] BIOCOMPATIBLE BLOCK COPOLYMER

[75] Inventors: Peter Neuenschwander, Haegelerstrasse 4, CH-5400 Baden; Georg K. Uhlschmid, Gladbachstrasse 104, CH-8044 Zurich; Ulrich W. Suter, Lavendelweg 8, CH-8050 Zurich; Gianluca Ciardelli, Zurich; Thomas Hirt, Gommiswald; Olivier Keiser, Zurich, all of Switzerland; Kazushige Kojima, Nagoya, Japan; Andreas Lendlein, Siershahn, Germany; Sandro Matter, Zofingen, Switzerland

[73] Assignees: Peter Neuenschwander, Baden; Georg K. Uhlschmid; Ulrich W. Suter, both of Zurich, all of Switzerland

[21] Appl. No.: 513,399

[22] Filed: Aug. 10, 1995

[30] Foreign Application Priority Data

Aug. 10, 1994 [CH] Switzerland ............. 02 478/94

[51] Int. Cl.$^6$ ............. C08G 18/42; C08G 63/672; C08G 63/06
[52] U.S. Cl. ............. 525/415; 525/419; 525/440; 525/450
[58] Field of Search ............. 525/415, 419, 525/450, 440

[56] References Cited

U.S. PATENT DOCUMENTS 3,663,515  5/1972  Hostettler et al. ............. 525/440
4,281,077  7/1981  Hirzy ............. 525/179

FOREIGN PATENT DOCUMENTS 0 295 055  12/1988  European Pat. Off.
0 552 896  7/1993  European Pat. Off.
42 24 401  1/1994  Germany.
2 067 580  7/1981  United Kingdom.

OTHER PUBLICATIONS

James J. O'Malley, "Crystalline Isomeric Polyester Block Copolymers. Scanning Calorimetry and Density Measurements", *Journal of Polymer Science*, vol. 13, 1975, pp. 1353–1363.

G.J.M deKoning et al., "A biodegradable rubber by crosslinking poly(hydroxyalkanoate) from Pseudomonas oleovorans", *Polymer*, vol. 35, No. 10, 1994, pp. 2090–2097.

S.C. Woodward et al., "The intracellular degradation of poly(ε–caprolactone)", *Journal of Biomedical Materials Research*, vol. 19, 1985, pp. 437–444.

A. Schindler et al., "Biodegradable Elastomeric Polyesters", *ACS Polymer Preprints*, vol. 23, No. 2, 1982, pp. 111–113 & 116.

C.G. Pitt et al., "Aliphatic Polyesters. I. The Degradation of Poly(ε–caprolactone) In Vivo", *Journal of Applied Polymer Science*, vol. 26, 1981, pp. 3779–3787.

Y. Hori et al., "A Novel Biodegradable Poly(urethane ester) Synthesized from Poly(3–hydroxybutyrate) Segments", *Macromolecules*, vol. 25, No. 19, 1992, pp. 5117–5118.

D.F. Williams et al., "The Degradation of Polyhydroxybutyrate (PHB)", *Biomaterials and Clinical Applications*, 1987, pp. 471–476.

S.J. Holland et al., "Polymers for biodegradable medical devices, II. Hydroxybutyrate–hydroxyvalerate copolymers: hydrolytic degradation studies", *Biomaterials*, vol. 8, Jul. 1987, pp. 289–295.

S.J. Holland et al., "Polymers for biodegradable medical devices, VII. Hydroxybutyrate–hydroxyvalerate copolymers: degradation of copolymers and their blends with polysaccharides under in vitro physiological conditions", *Biomaterials*, vol. 11, Apr. 1990, pp. 206–215.

M.S. Reeve et al., "The Preparation and Characterization of [R]–Poly(β–Hydroxybutyrate)–Poly(ε–Caprolactone) and [R]–Poly(β–Hydroxybutyrate)–Poly(Lactide) Degradable Diblock Copolymers", *Polym. Mat. Sci. Eng.* vol. 67, 1992, pp. 182–183.

M.S. Reeve et al., "Thermal and Crystalline Studies of [R]–Poly(β–Hydroxybutyrate)–Poly(ε–Caprolactone) and [R]–Poly(β–Hydroxybutyrate)–Poly(Lactide) Degradable Diblock Copolymers", *Polym. Mat. Sci. Eng.*, vol. 67, 1992, pp. 232–234.

T. Saito et al., "In vivo and in vitro degradation of poly(3–hydroxybutyrate) in rat", *Biomaterials*, vol. 12, Apr. 1991, pp. 309–312.

J.C. Knowles et al., "In vitro degradation of a PHB/PHV copolymer and a new technique for monitoring early surface changes", *Biomaterials*, vol. 12, Mar. 1991, pp. 210–215.

C. Doyle et al., "In vitro and in vivo evaluation of polyhydroxybutyrate and of polyhydroxybutyrate reinforced with hydroxyapatite", *Biomaterials*, vol. 12, Nov. 1991, pp. 840–847.

T. Kissel et al., "Properties of block– and random–copolymers of lactic acid and glycolic acid", *Proceed. Intern. Symp. Control. Rel. Bioact. Mater.*, vol. 20, 1993, pp. 127–134.

P. Cerrai et al., "Block Copolymers of L–Lactide and Poly(Ethylene Gycol)Obtained By Non–Catalyzed Synthesis", *10th European Conference on Biomaterials*, Davos, Switzerland, Sep. 8–11, 1993, p. 20.

Ph. Dubois et al., "Macromolecular Engineering of Polylactones and Polylactides. 11. Synthesis and Use of Alkylaluminum Dialkoxides and Dithiolates as Promoters of Hydroxy Telechelic Poly(ε–caprolactone) and α, ω–Dihydroxy Triblock Copolymers Containing Outer Polyester Blocks", *Macromolecules*, vol. 26, 1993, pp. 2730–2735.

Y. Kumagai, et al "Synthesis of Block Copolymers of Poly(3–Hydroxybutyrate) and Poly(Ethylene Glycole)", J. of Env. Polym. Degr. v1, n.2, 1993, pp. 81–87.

Primary Examiner—Irina S. Zemel
Attorney, Agent, or Firm—Oblon, Spivak, McClelland, Maier & Neustadt, P.C.

[57] ABSTRACT

The biocompatible multi-block copolymer is obtainable by linear polycondensation of at least two α,ω-dihydroxypolyesters acid and/or α,ω-dihydroxypolyethers with a diisocyanate, diacid halide or phosgene. The block copolymer is preferably degradable in the human or animal body. The block copolymer is suitable for the production of medical implants and surgical aids.

24 Claims, No Drawings

BIOCOMPATIBLE BLOCK COPOLYMER

BACKGROUND OF THE INVENTION

1. Field of the Invention

The invention relates to a biocompatible block copolymer, a medical implant which has been produced with the block copolymer, use of the block copolymer for the production of a medical implant, and new α,ω-dihydroxypolyesters for the preparation of the block copolymer. Where the term medicine in used, this is understood as meaning both human and veterinary medicine.

2. Discussion of the Background

The number of biocompatible polymers for medical implants employed in practice is surprisingly small. Apart from the problem of compatibility, this can be attributed on the one hand to the high technical requirements with respect to mechanical strength, sterilizability, biological degradability and the like, and on the other hand to the large number of different administrative regulations in individual countries.

For example, vascular prostheses, i.e. tubular implants having a diameter of about 1 to 6 mm, of nonabsorbable materials such as Dacron, polytetrafluoroethylene and the like are employed for arterial or venous vessel replacements. These vascular prostheses have several adverse effects on their environment. Above all, the adverse change at the anastomosis, i.e. the connecting point with the endogenous vessels, practically cannot be influenced. Regeneration of a functional vascular wall in the region of the known implants is not possible. A covering with functional vascular cells for avoiding a thrombotic occlusion during long-term use occurs, if at all, only under systemic anticoagulation. Known vascular prostheses are consequently foreign bodies, the physical and biological properties of which practically cannot be influenced.

An attempt has been made to influence the biological properties of vascular prostheses by coating with heparin or heparinoids. However, these coatings have only a temporally limited action in qualitative respects.

Polyester diols derived from caprolactone which are employed in the production of biomedical separating devices are known from GB-A 2 067 580.

Block copolyesters and block courethanes which are suitable as plasticizers for PVC are known from U.S. Pat. No. 4,281,077.

J. Polym. Sci. 13(7) 1353–63 (1975) describes block copolyesters with a crystallizine and an amorphous block.

U.S. Pat. No. 3,663,515 describes the preparation of polyesters and polyurethanes based on a polyester diol from caprolactones.

DE-A1 42 24 401 describes a process in which biologically degradable polyesters are cleaved with polyfunctional compounds. The cleavage products are modified by polycondensation.

EP-A1 0 552 896 describes optically active biologically degradable block polymers which are built up only from one chemical type of block unit.

EP-A2 0 295 055 discloses biologically degradable block copolymers which contain only L-lactic acid as the block unit.

SUMMARY OF THE INVENTION

One object of the present invention is to provide a new polymer having improved biological and processing properties.

This aim is achieved by the copolymer of the invention.

DETAILED DESCRIPTION OF THE PREFERRED EMBODIMENTS

The biocompatible multi-block copolymer of the invention is built up from at least three components and has at least two chemically different block units which are joined to one another by means of diisocyanate, diacid halide or phosgene by linear polycondensation. The block units, i.e. the α,ω-dihydroxypolyester and α,ω-dihydroxypolyether, are also called macrodiols and oligomers in the following description. Polyurethanes are obtained by linking the macrodiols with diisocyanate, polyesters by linking the macrodiols with diacid halide and polycarbonates by linking the macrodiols with phosgene.

One of the block units is an α,ω-dihydroxypolyester which is obtained by transesterification of poly-(R)-(3)-hydroxybutyric acid, or copolymers thereof with 3-hydroxyvaleric acid with ethylene glycol.

Other macrodiols which are suitable for the preparation of the multi-block copolymers according to the invention are, in particular, a new group of α,ω-dihydroxypolyesters based on oligomers of α-, β-, γ- and ω-hydroxycarboxylic acids and co-oligomers thereof, which are obtained by ring-opening polymerization of cyclic esters or lactones. Preferred cyclic esters of this type are (L,L)-dilactide, (D,D)-dilactide, (D,L)-dilactide, diglycolide or the preferred lactams β-(R)-butyrolactone, β-(S)-butyrolactone, β-rac-butyrolactone and ε-caprolactone or mixtures thereof. The ring opening is carried out with aliphatic diols, such as ethylene glycol or longer chain alkylene diols, for example alkylene diols having 3–10 carbon atoms. The molecular weight of the resulting macrodiol is determined by the amount of diols.

The ring-opening polymerization of the cyclic esters or lactones in preferably carried out in bulk (neat) in the presence of a catalyst, for example $SnO(Bu)_2$, at 100° C. to 160° C. The resulting macrodiols have molecular weights of about 300 to 10,000 Daltons. The macrodiols prepared from mixtures of cyclic esters or lactones have a microstructure, depending on the amount of catalyst, in which the distribution of the monomeric components between the block form is random or alternating. The macrodiols and the block copolymers prepared therefrom have different physical properties, depending on these distribution characteristics.

Examples of macrodiols which are obtained by ring-opening polymerization of cyclic esters or lactones in the presence of a catalyst and can be used for preparation of the block copolymers according to the invention are described below under a) to c).

The nomenclature used here is based on W. V. Metanomski, Compendium of Macromolecular Nomenclature, Blackwell Scientific Publications (1991). Any mention of a "ran" distribution also includes the distributions referred to by the term "stat".

The letters m, n, p, q, r and s in the formula a) to e) are 0 or an integer from preferably 1 to 50.

a) Homomacrodiols

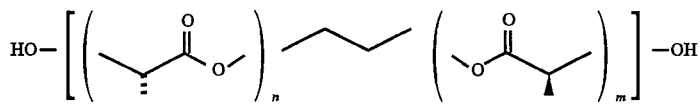

α,ω-Dihydroxy-(poly(L-lactide)-ethylene-poly(L-lactide)) (I)

b) Co-macrodiols from the racemate of a lactone

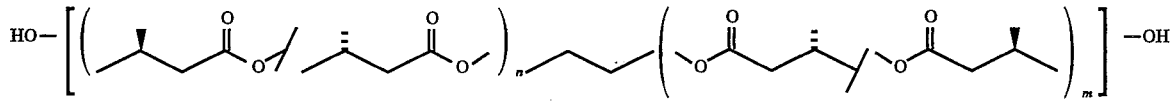

α,ω-Dihydroxy-(oligo(3-(R)-hydroxybutyrate-ran-3-(S)-hydroxybutyrate)-ethylene-oligo(3-(R)-hydroxybutyrate-ran-3-(S)-hydroxybutyrate)) (II)

c) Co-macrodiols which are prepared by copolymerization of two or more different lactones and/or cyclic diesters.

$c_1$) Macrodiols, the microstructure of which has been influenced by the amount of catalyst:

$c_2$) Macrodiols, the microstructure of which is not influenced by the amount of catalyst:

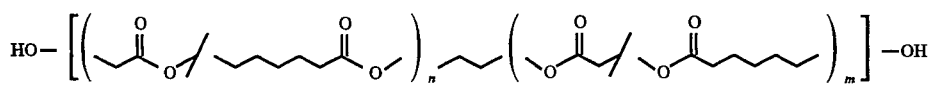

α,ω-Dihydroxy-(oligo(glycolide-ran-ε-caprolactone)-ethylene-oligo(glycolide-ran-ε-caprolactone)) (III)

α,ω-Dihydroxy-(oligo(L-lactide-ran-ε-caprolactone)-ethylene-oligo(L-lactide-ran-ε-caprolactone)) (IV)

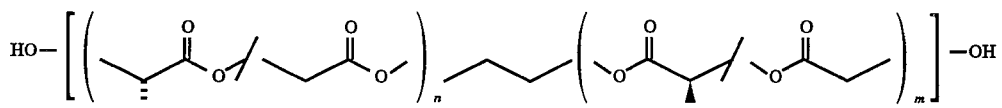

α,ω-Dihydroxy-(oligo(L-lactide-ran-glycolide)-ethylene-oligo(L-lactide-ran-glycolide)) (V)

α,ω-Dihydroxy-(oligo(3-(R)-hydroxybutyrate-ran-3-(S)-hydroxybutyrate-ran-glycolide)-ethylene-oligo(3-(R)-hydroxybutyrate-ran-3-(S)-hydroxybutyrate-ran-glycolide)) (VI)

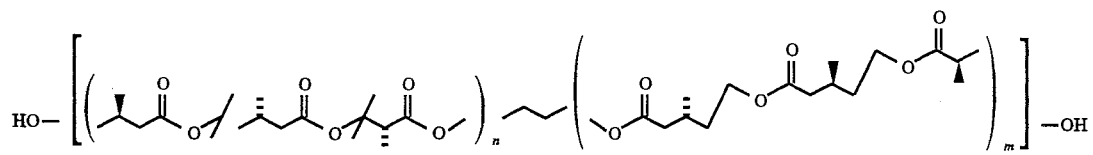

α,ω-Dihydroxy-(oligo(3-(R)-hydroxybutyrate-ran-3-(S)-hydroxybutyrate-ran-L-lactide)-ethylene-oligo(3-(R)-hydroxybutyrate-ran-3-(S)-hydroxybutyrate-ran-L-lactide)) (VII)

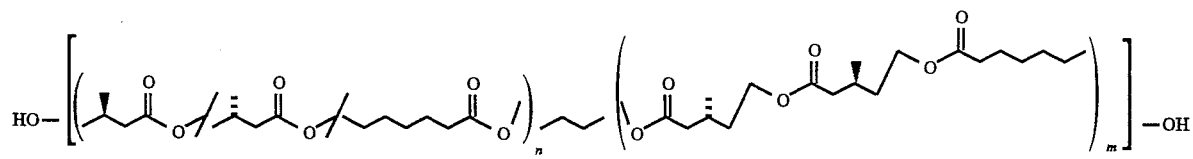

α,ω-Dihydroxy-(oligo(3-(R)-hydroxybutyrate-ran-3(S)-hydroxybutyrate-ran-ε-caprolactone)-ethylene-oligo(3-(R)-hydroxybutyrate-ran-3-(S)-hydroxybutyrate-ran-ε-caprolactone)) (VIII)

The ring-opening polymerization for the preparation of macrodiols can also be carried out without a catalyst. The macrodiols shown below were prepared from (L,L)-dilactide, diglycolide and ε-caprolactone by ring-opening polymerization in bulk at 100° C. to 160° C. without a catalyst. They have a molecular weight on the order of 300 to 10,000 Daltons. Also, a microstructure, i.e. a characteristic distribution of the monomers in the polymer, is found, the physical properties depending on the distribution statistics.

d) Homomacrodiols

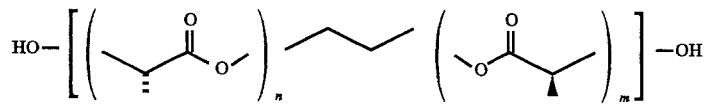

α,ω-Dihydroxy-(poly(L-lactide)-ethylene-poly(L-lactide)) (IX)

e) Comacrodiols with a block structure

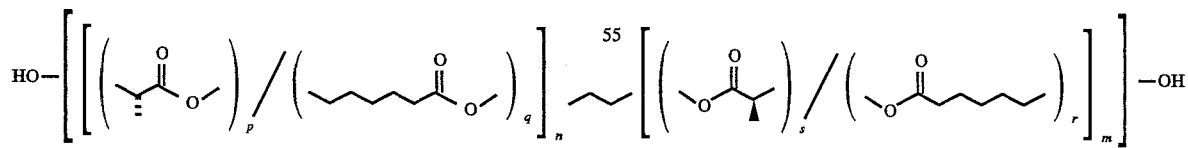

α,ω-Dihydroxy-(oligo(L-lactide-block-ε-caprolactone)-ethylene-oligo-(L-lactide-block-ε-caprolactone)) (X)

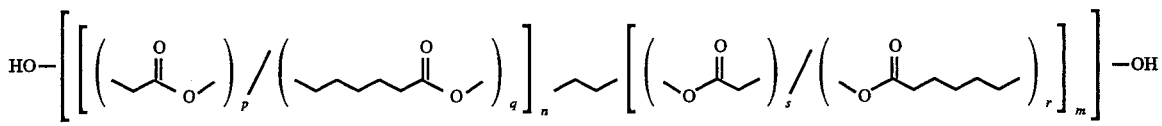

α,ω-Dihydroxy-(oligo(glycolide-block-ε-caprolactone)-ethylene-oligo(glycolide-block-ε-caprolactone)) (XI)

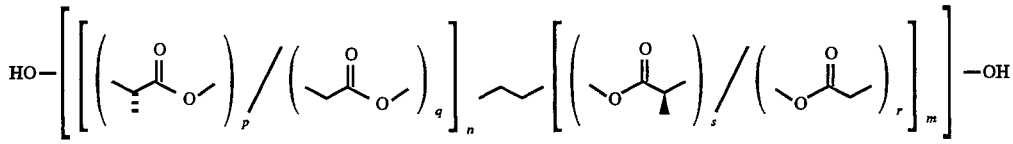

α,ω-Dihydroxy-(oligo(glycolide-block-L-lactide)-ethylene-oligo(glycolide-block-L-lactide)) (XII)

Alternatively, the macrodiol α,ω-dihydroxy-(oligo-(3-(R)-hydroxybutyrate)-ethylene-oligo(3-(R)-hydroxybutyrate)) can be prepared can be prepared by transesterification of poly((R)-3-hydroxybutyric acid) with ethylene glycol, preferably in a high concentration in diglyme at 135° C. in the presence of dibutyltin dilaurate as a catalyst.

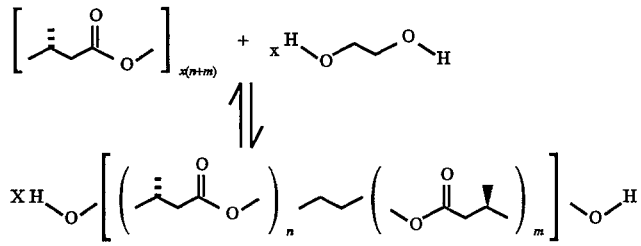

α,ω-Dihydroxy-(oligo-(3-(R)-hydroxybutyrate)-ethylene-oligo(3-(R)-hydroxybutyrate))

The copolymers of 3-(R)-hydroxybutyric acid and 3-hydroxyvaleric acid (Biopol with an HV content up to about 12%) can also be transesterified in the same manner.

Suitable diisocyanates for the preparation of the polyurethane embodiment of the block copolymers according to the invention are, in particular, hexamethylene diisocyanate, 2,2,4-trimethylhexamethylene diisocyanate, cyclohexyl-1,4-diisocyanate, cyclohexyl-1,2-diisocyanate, isophorone diisocyanate, methylenedicyclohexyl diisocyanate and L-lysine diisocyanate methyl ester.

The diacid halides of oxalic acid, malonic acid, succinic acid, glutaric acid, adipic acid, pimelic acid, suberic acid, azelaic acid, trimethyladipic acid, sebacic acid, dodecanedioic acid, tetradecanedioic acid and hexadecanedioic acid are particularly suitable for the preparation of the polyester embodiment of the block copolymers according to the invention.

The block copolymers according to the invention are built up from two types of macrodiols, i.e. block units, one macrodiol preferably forming crystalline regions in the block copolymer and the other macrodiol preferably forming amorphous regions in the polymer. The macrodiols which form crystalline regions in the block copolymer are those which are crystallizable compounds, and the macrodiols which form amorphous regions can be crystallizable or non-crystallizable compounds.

The block copolymers according to the invention can comprise other co-condensed low molecular weight compounds. These have one or more other functional groups, in addition to the reactive groups required for the linear cocondensation, which are preferably OH or $NH_2$ groups.

These functional groups can be protected or unprotected reactive groups, or groups which impart certain use properties to the block copolymers. For example, these functional groups can enable the block copolymers to be used as X-ray contrast media or as agents for increasing contrast in other diagnostic methods, such as computerized tomography (CT) and magnetic resonance (MR).

If the functional groups are reactive groups, they allow covalent bonding of active compounds to the block copolymer according to the invention. Such active compounds are, for example, diagnostics, such as contrast media, pharmaceutically active compounds, peptides, proteins and the like.

Particularly suitable low molecular weight comonomers are:

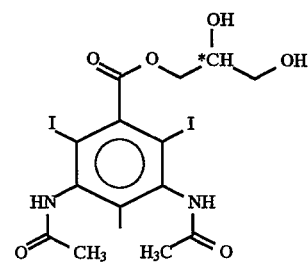

diatrizoic acid monoglyceryl ester:

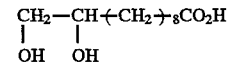

-continued 10,11-dihydroxyundecanoic acid

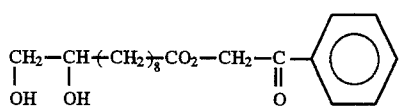

phenacyl-10,11-dihydroxyundecanoate

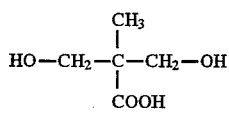

2,2-bis-(hydroxymethyl)-propionic acid

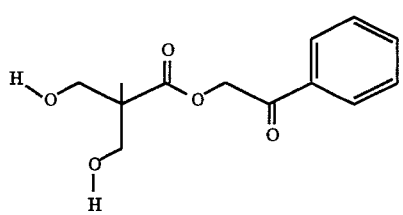

phenacyl-bis-(hydroxymethyl)-propionate

For example, the antibiotic doxorubicin can be bonded to a block copolymer which carries acid groups in the side chains and is obtained by cocondensation of two macrodiols with phenacyl-10,11-dihydroxyundecanoate and elimination of the phenacyl protective group. The acid group can be activated here in a homogeneous organic solution by the Steglich reagent or dicyclohexylcarbodiimide.

For covalent bonding of the peptide RGDS to a block copolymer according to the invention, a water-soluble carbodiimide can be employed as an activator in a heterogeneous system of water/solid block copolymer.

The block copolymers of the invention are soluble in organic solvents and have the particular advantage that their physical, chemical and biological properties can be adjusted within a wide spectrum by varying the units. The block copolymers can thus be adapted to the particular specific use. For example, the block copolymers, as is shown in the examples, can be biologically degradable, even in the human or animal body. The property mentioned last is particularly important for use of the block copolymers for medical implants.

Another important property of the block copolymers of the invention is their thermoplastic processability as a result of the linear linking of the base units. In general, the block copolymers can be processed at temperatures between 80° C. and 200° C., preferably between 100° C. and 140° C. For medical implants, this temperature range provides the advantage of adaptability of the shape and size of the implant. Surgical suture material furthermore can be welded, which enables complicated linking to be dispensed with.

The implants can also be in the form of a tube. A tube is also to be understood as meaning hoses. The tubes can have circular, elliptical and polygonal cross-sections, it also being possible for several channels to be arranged within a tube. Regeneration of a functional vascular wall or of a nerve can take place with the implants according to the invention. A thrombotic occlusion during long-term use can be avoided by a covering with functional vascular cells. For certain uses, the implant material, i.e. the block copolymer, can have a porous structure. It can also have a capsule form for accommodating pharmaceutical active compounds or diagnostics also in the form of particles.

Some uses of the block copolymers according to the invention in the medical sector are described below. Further uses are of course possible.

Production of tubular structures (vessel replacements, trachea replacements, replacement of other biological tube structures) in solid, spiral-shaped, flexible, expandable, self-expanding, braided and tricot form, which can be sufficiently physically and pharmacologically structured or coated on the inside or outside according to the biological and functional requirements. The pharmacological substances are held on the block copolymer either by absorption or by covalent chemical bonding. Production of stents (rigid, expandable, self-expanding) for vessels or other biological tube structures (esophagus, biliary tract, urinary tract).

Production of film-like structures (wound covering, membrane oxygenators, cornea replacement base and the like).

Production of thread-like structures (surgical suture material, base for woven, braided or tricot structures).

Production of clip-like or clamp-like structures for clamp suture apparatuses, clamps for ligature of small blood vessels and utilization of the thermoplastic properties for closure.

Production of solid to gelatinous or porous structures as a matrix for the production of simple or composite biological tissues in vitro (tissue engineering) or in vivo (preconditioned spacers for skin replacements, fatty tissue, tendons, cartilage and bone, nerves and the like). Use in topical wound treatment.

Production of polymeric structures which, on the basis of the physical or biological charge properties and physical structures (foams, gel, micronanospheres) and the surface structure, allow release therapeutically (hormones, medicaments) or cosmetically (liposomes, proteins, vitamins and the like) via internal anatomical structures or via the skin.

Use for sclerosing varicoceles, varices of the legs (esophageal varices) or gastrointestinal sources of hemorrhage (endoscopically or transvascularly).

Production of polymeric structures which, in a suitable form and with suitable charging with bioactive substances, allow reversible or irreversible contraception by blocking (oviduct, ductus spermaticus).

Production of artificial auditory ossicles.

Use of the block copolymer as a base for culture of corneal corpuscles on films for transplantation as cornea replacements.

Use of the block copolymer in an appropriate physical and/or biological form in medical, dental, micro- or nano-technology.

Use in a form which can be employed therapeutically and/or diagnostically in imaging processes (X-ray, CT, NMR, chemoembolization, PET, microscopy). The block copolymers according to the invention can be processed by extrusion or injection molding by known processes. Films can also be produced by compression molding. Open-pored structures can be produced by various known processes, such as dipcoating or phase inversion or addition of salt to a solution of the block copolymer and precipitation of the polymer.

The mechanical properties of the block copolymers according to the invention depend greatly on the choice of crystalline component, the molecular weight and weight content thereof, and the choice of non-crystalline component. The block copolymers can have an E modulus from 5 MPa to 2 GPa, depending on their composition. Tear strengths of 5 to 20 MPa and elongations at break of 20 to 900% have been observed. The surface energies also depend an the composition of the copolymers. The contact angle with water, i.e. the measure of the surface energy, is between 60° and 85°, i.e. in a range which is favorable for cell adhesion and protein binding. Polymers which carry carboxyl groups have shown contact angles of between 40° and 70°.

The absorption of water by the block copolymers also depends on their composition. It is in general between 0.2 and 5%, but can also be higher in individual cases.

The block copolymers according to the invention are sensitive to hydrolysis. The molecular weight decreases during storage in a buffer solution at 37° C. The rate of degradation increases with a pH of the buffer solution deviating from pH=7, or also with increasing temperature.

The block copolymers according to the invention have proved to be biocompatible in cell cultures in vitro with macrophages and fibroblasts on the basis of the observation of cell adhesion, cell growth, cell vitality and cell activation as well as production of extracellular proteins and cytokines. With the aid of in vivo studies on rats in short-, medium- and long-term studies of subcutaneous implantation of films and gels, only mild foreign body reactions or encapsulation of the implants were observed. The block copolymers according to the invention are consequently found to be biocompatible.

In long-term studies in vivo, the block copolymers proved to be biodegradable. The degradation rates depend greatly on the particular composition and structure.

The invention is illustrated further with the aid of non-limiting examples below.

The formula of the compounds of the examples are shown on sheets of formula. In the formula, the letters m, m', n, n', p, p', q, q', r, r', s, s', t and u are 0 or an integer, preferably from 1 to 50. x is an integer, preferably from 1 to 100.

EXAMPLES

Example 1—Preparation of α,ω-dihydroxy-(oligo(3-(R)-hydroxybutyrate-ethylene-oligo-(3-(R)-hydroxybutyrate)) by transesterification of poly((R)-3-hydroxybutyrate) with ethylene glycol.

1055 g of poly((R)-3-hydroxybutyrate)/BIOPOL (ICI) were dissolved in 3 liters of diglyme at 140° C. under $N_2$. 246 g of ethylene glycol and 5.21 g of dibutyltin dilaurate (catalyst) were then added. 1.5 g (125° C.) of catalyst were added after 1 hour, and a further 1.2 g of catalyst were added after a further 2.5 hours. The degradation was monitored continuously by GPC measurements and an additional 0.6 g of catalyst was added at intervals of 1 hour until the required molecular weight of the degradation product was achieved. Monitoring of the molecular weight was by GPC. The degradation was discontinued by precipitation of the polymer in 10 liters of water.

The degraded oligomer was filtered off and suspended in about 6 to 7 liters of distilled water and filtered off again after 20 hours a total of 5 times. After the last washing operation, the granular oligomer was sucked dry for 1 hour and then dried in 2 large crystallizing dishes first in a drying cabinet at 50° C. in vacuo. It was then dried further under a high vacuum ($10^{-2}$ bar) for 30 hours in a drying cabinet at 60° C.

The dry oligomer was then dissolved in methylene chloride so that a 30–35% solution resulted. The slightly warmed solution was then filtered over a quartz sand bed on a glass suction filter. The filtrate was purified by chromatography over a silica gel 60 column. Column height was about 15 cm, diameter was 3 cm. The filtrate was concentrated until oligomers started to precipitate out at 35° C. The solution (4.5 liter) was then poured into 10 liters of petroleum ether 30/50 so that the oligomer precipitated out.

The precipitate was filtered off and dried.

Yield=86% of oligomer ($M_n$=2450)

Preparation of Macrodiols from Lactones Using a Catalyst

Example 2—Homooligomers: Preparation of α,ω-dihydroxy-(poly(L-lactide)ethylene-poly(L-lactide)) from L,L-dilactide (semimicro batch)

14.4 g (0.1 mol) of L,L-dilactide, 186 mg (3 mmol) of ethylene glycol and 25 mg (0.1 mmol) of dibutyltin oxide were heated at 120° C. in a 100 ml two-necked flask under $N_2$ (quality 5.0) for 60 minutes.

Preparation of α,ω-dihydroxy-(poly(L-lactide)-ethylene-poly(L-lactide)) from L,L-dilactide (macro batch)

100.8 g (0.7 mol) of L,L-dilactide, 1.30 g (21 mmol) of ethylene glycol and 0.19 g (0.8 mmol) of dibutyltin oxide were heated at 120° C. in a 500 ml two-necked flask under $N_2$ (quality 5.0) for 60 minutes.

Work Up

The reaction mixture was dissolved in 20 ml (macro batch: 200 ml) of 1,2-dichloroethane and purified by chromatography over a silica gel column 20–25 cm long. The column was prepared with petroleum ether. 1,2-dichloroethane was used as the mobile phase. After the solvent had been concentrated, the residue was precipitated in a five-fold volume excess of petroleum ether and then washed twice with petroleum ether. The product was dried at 80° C. under house vacuum for 3 days and then under a high vacuum for one day.

Example 3—Macrodiols prepared from the racemate of a lactone

Preparation of α,ω-dihydroxy-(oligo(3-(R)-hydroxybutyrate-ran-3-(S)-hydroxybutyrate)-ethylene-oligo (3-(R)-hydroxybutyrate-ran-3-(S)-hydroxybutyrate)) from rac-β-butyrolactone (semimicro batch)

8.609 g (0.1 mol) of rac-β-butyrolactone, 182 mg (2.9 mmol) of ethylene glycol and 500 mg (2.0 mmol) of dibutyltin oxide were heated at 135° C. in a 100 ml two-necked flask under $N_2$ (quality 5.0) for 120 minutes.

Preparation of α,ω-dihydroxy-(oligo(3-(R)-hydroxybutyrate-ran-3-(S)-hydroxybutyrate)-ethylene-oligo (3-(R)-hydroxybutyrate-ran-3-(S)-hydroxybutyrate)) from rac-β-butyrolactone (macro batch) 60.3 g (0.7 mol) of rac-β-butyrolactone, 1.30 g (21 mmol) of ethylene glycol and 0.20 g (0.8 mmol) of dibutyltin oxide were heated at 135° C. in a 500 ml two-necked flask under $N_2$ (quality 5.0) for 120 minutes.

Work Up

The reaction mixture was dissolved in 20 ml (macro batch: 200 ml) of 1,2-dichloroethane and purified by chromatography over a silica gel column 20–25 cm long. The column was prepared with petroleum ether. 1,2-dichloroethane was used as the mobile phase. After the solvent had been distilled off, the residue was precipitated in a five-fold volume excess of petroleum ether and then washed twice with petroleum ether. The product was dried at 80° C. under house vacuum for 3 days and then under a high vacuum for three days.

Example 4—Macrodiols, prepared from two or more lactones

Preparation of α,ω-dihydroxy-(oligo(glycolide-ran-ε-caprolactone)-ethylene-oligo(glycolide-ran-ε-caprolactone)) from diglycolide and ε-caprolactone (semimicro batch)

2.9 g (0.025 mol) of diglycolide, 5.7 g (0.05 mol) of ε-caprolactone, 186 mg (3mmol) of ethylene glycol and 25 mg (0.1 mmol) of dibutyltin oxide were heated at 140° C. in a 100 ml two-necked flask under $N_2$ (quality 5.0) for 30 minutes.

Preparation of α,ω-dihydroxy-(oligo(glycolide-ran-ε-caprolactone)-ethylene-oligo(glycolide-ran-ε-caprolactone)) from diglycolide and ε-caprolactone (macro batch)

20.3 g (0.175 mol) of diglycolide, 40.0 g (0.35 mol) of ε-caprolactone, 1.30 g (21 mmol) of ethylene glycol and 174 mg (0.7 mmol) of dibutyltin oxide were heated at 140° C. in a 500 ml two-necked flask under $N_2$ (quality 5.0) for 30 minutes.

Work Up

The reaction mixture was dissolved in 20 ml (macro batch: 200 ml) of 1,2-dichloroethane and purified by chromatography over a silica gel column 20–25 cm long. The column was prepared with petroleum ether. 1,2 dichloroethane was used as the mobile phase. After the solvent had been distilled off, the residue was precipitated in a five-fold volume excess of petroleum ether and then washed twice with petroleum ether. The product was dried at 80° C. under house vacuum for 3 days and then under a high vacuum for 3 days.

Preparation of macrodiols without a catalyst (Examples 5–6)

Example 5—Homooligomers: Preparation of α,ω-dihydroxy-(poly(L-lactide)-ethylene-poly(L-lactide)) from L-L-dilactide (semimicro batch)

14.4 g (0.1 mol) of L,L-dilactide and 186 mg (3 mol) of ethylene glycol were heated at 120° C. in a 100 ml two-necked flask under $N_2$ (quality 5.0) for 3 days.

Preparation of α,ω-dihydroxy-(poly(L-lactide)-ethylene-poly(L-lactide)) from L-L-dilactide (macro batch)

70.6 g (0.7 mol) of L,L-dilactide and 1.30 (21 mmol) of ethylene glycol were heated at 120° C. in a 500 ml two-necked flask under $N_2$ (quality 5.0) for 3 days.

Work Up

The reaction mixture was dissolved in 20 ml (macro batch: 200 ml) of 1,2-dichloroethane. The product was then precipitated in a five-fold volume excess of petroleum ether at 0° C. and washed twice with petroleum ether. It was dried at 80° C. under house vacuum for 3 days and then under a high vacuum for one day.

Example 6—Macrodiols having a block structure prepared from two or more different lactones Preparation of α,ω-dihydroxy-(oligo(glycolide-block-ε-caprolactone)-ethylene-oligo(glycolide-block-ε-caprolactone)) from diglycolide and ε-caprolactone (semimicro batch)

2.9 g (0.025 mol) of diglycolide, 5.7 g (0.05 mol) of ε-caprolactone and 186 mg (3 mmol) of ethylene glycol were heated at 140° C. in a 100 ml two-necked flask under $N_2$ (quality 5.0) for 3 days.

Preparation of α,ω-dihydroxy-(oligo(glycolide-block-ε-caprolactone)-ethylene-oligo(glycolide-block-ε-caprolactone)) from diglycolide and ε-caprolactone (macro batch)

20.3 g (0.0175 mol) of diglycolide, 40.0 g (0.035 mol) of ε-caprolactone and 1.3 mg (21 mmol) of ethylene glycol were heated at 140° C. in a 500 ml two-necked flask under $N_2$ (quality 5.0) for 3 days.

Work Up

The reaction mixture was dissolved in 20 ml (macro batch: 200 ml) of diglyme at 140° C. The product was then precipitated out in a five-fold volume excess of petroleum ether at 0° C. and washed twice with petroleum ether. It was dried at 80° C. under house vacuum for 3 days and then under a high vacuum for one day.

Example 7—Macrodiols from polyetherdiol and diglycolide (without a catalyst)

Preparation of α,ω-dihydroxy-(oligo(glycolide)-poly(tetrahydrofuran)oligo(glycolide)) from poly(tetrahydrofuran) and diglycolide.

Drying of poly(tetrahydrofuran)

50 g (0.077 mol) of poly(tetrahydrofuran) (Mn=650) were dissolved in 100 ml of 1,2-dichloroethane and dried in a Soxhlet extractor charged with Å4 molecular sieves. The molecular sieve was replaced after every 2 to 3 hours of drying. The procedure was carried out under nitrogen. After drying, the solvent was distilled off.

Polymerization with diglycolide 50 g (0.077 mol) of poly(tetrahydrofuran) (Mn=650) and 4.47 g (0.077 mol) of diglycolide were heated at 135° C. in a 250 ml two-necked flask under nitrogen for 3 days.

Work Up

The reaction mixture was reprecipitated from a solution with predried 1,2-dichloroethane in hexane.

Example 8—Macrodiols from polyetherdiol and diglycolide (with a catalyst)

Preparation of α,ω-dihydroxy-(oligo(glycolide)-poly(tetrahydrofuran)oligo(glycolide)) from poly(tetrahydrofuran) and diglycolide with a catalyst Drying of poly(tetrahydrofuran)

50 g (0.077 mol) of poly(tetrahydrofuran) (Mn=650) were dissolved in 100 ml of 1,2-dichloroethane and dried in a Soxhlet extractor charged with A4 molecular sieves. The molecular sieve was replaced after every 2 to 3 hours of drying. The procedure was carried out under nitrogen. After drying, the solvent was distilled off.

Polymerization with diglycolide 50 g (0.077 mol) of poly(tetrahydrofuran) (Mn=650), 4.47 g (0.077 mol) of diglycolide and 75 mg (0.3 mmol) of dibutyltin oxide were heated at 135° C. in a 250 ml two necked flask under nitrogen for 15 minutes.

Work Up

The reaction mixture was dissolved in 100 ml of 1,2-dichloroethane (predried) and purified by chromatography over a silica gel column 20 to 25 cm long. The column was prepared with petroleum ether. 1,2-Dichloroethane was used as the mobile phase. After the solvent had been concentrated, the product was precipitated out in a five-fold excess of petroleum ether. It was dried at 40° C. under house vacuum for 3 days and then under a high vacuum for one day.

Definitions:

HG3000 (crystallizing segment)*

α,ω-Dihydroxy-(oligo(glycolide-block-ε-caprolactone)-ethylene-oligo(glycolide-block-ε-caprolactone)), cf. 1-b-2, with a molecular weight M=2479 g-mol$^{-1}$ (VPO) and a molar ratio n(glycolide): n(ε-caprolactone) of 2:1.

SG3000 (non-crystallizing segment)*

α,ω-Dihydroxy-(oligo(glycolide-ran-ε-caprolactone)-ethylene-oligo(glycolide-ran-ε-caprolactone)), cf. 2-b-1, with a molecular weight M=2475 g-mol$^{-1}$ (VPO) and a molar ratio n(glycolide): n(ε-caprolactone) of 1:1.

SG500 (non-crystallizing segment)*

α,ω-Dihydroxy-(oligo(glycolide-block-ε-caprolactone)-ethylene-oligo(glycolide-block-ε-caprolactone)), cf. 1-b-2, with a molecular weight M=475 g-mol$^{-1}$ (VPO) and a molar ratio n(glycolide): n(ε-caprolactone) of 0.85:0.15

PHB-diol (crystallizing segment)*

α,ω-Dihydroxy-(oligo(3-(R)-hydroxybutyrate)-ethylene-oligo(3-(R)-hydroxybutyrate)) with a molecular weight $M_n$=2300 g-mol$^{-1}$ (VPO)

PHB/HV-diol (crystallizing segment)*

α,ω-Dihydroxy-(oligo(3-(R)-hydroxybutyric acid-co-3-(R)-hydroxyvaleric acid)-ethylene-oligo(3-(R)-hydroxybutyric acid-co-3-(R)-hydroxyvaleric acid)), prepared from BIOPOL with 4% of hydroxyvaleric acid. $M_n$=2300 g-mol$^{-1}$.

PCL-diol (crystalline segment, present in amorphous form in the block copolymer)*

α,ω-Dihydroxy-poly(ε-caprolactone)-ethylene-oxyethylene-poly(ε-caprolactone)) with a molecular weight M=1200 g-mol$^{-1}$ (VPO)

DIOREZ (Manufacturer: Macpherson Polymers) (non-crystallizing segment)*

α,ω-Dihydroxy-<oligo(adipic acid-alt-(butanediol; diethylene glycol; ethylene glycol))>.

PTHF-diol (non-crystallizing segment)*

α,ω-Dihydroxy-poly(tetramethylenoxy)ethylene-poly(tetramethylenoxy)) with a molecular weight M=650 g-mol$^{-1}$ (VPO)

Lysine methylester diisocyanate=2,6-diisocyanatocaproic acid methylester (LDI)

2,2,4-Trimethylhexamethylene 1,6-diisocyanate=isomer mixture 2,2,4/2,4,4 isomer-1:1 (TMDI) * at room temperature Example 9—Preparation of poly((α,ω-dihydroxy-<oligo(3-(R)-hydroxybutyric acid-co-3-(R)-hydroxyvaleric acid) ethylene-oligo(3-(R)-hydroxybutyric acid-co-3-(R)-hydroxyvaleric acid) >-alt-(2,2,4-trimethylhexamethylene-1,6-diisocyanate))-co-(α,ω-dihydroxy-<oligo(adipic acid-alt-(butanediol; diethylene glycol; ethylene glycol))>alt-(2,2,4-trimethylhexamethylene-1,6-diisocyanate))) (Formula 9 on the sheet of formulas)

25.18 g (11.00 mmol) of PHB/HV-diol and 25.177 g, (25.18 mmol) of DIOREZ were dissolved in 100 ml of 1,2-dichloroethane in a two-necked flask at 80° C. The solvent was then distilled off at an oil bath temperature of 110° C. until a slightly viscous, still stirrable solution remained in the flask and the water content of the last 10 ml of the distillate was 45 ppm. A stream of nitrogen was then passed over the apparatus. After the temperature of the oil bath had been reduced to 80° C., 7.5964 g (36.17 mmol) of 2,2,4-trimethylhexamethylene diisocyanate were added. To keep the stirrer moving, the mixture can be diluted with 1,2-dichloroethane. After a reaction time of 140, 167, 188 and 216 hours, 9.9, 14.3, 11.6 and 20 mg respectively (M=631.56 g/mol) of dibutyltin dilaurate were added from a 0.016M stock solution in 1,2-dichloroethane. After 220 hours, the reaction was stopped by precipitation of the polymer solution in low-boiling petroleum ether.

Purification:

The polymer was dissolved again in 1,2-dichloroethane and precipitated as a solution in low-boiling petroleum ether. Thereafter, the polymer was dissolved again in dioxane and filtered through a G4 suction filter, before the polymer from the dioxane solution was precipitated in slightly basic deionized water. The pH of the water was brought to 8–9 with sodium bicarbonate. Thereafter, the polymer was precipitated a second time from a dioxane solution in deionized water.

Example 10—Preparation of poly((α,ω-dihydroxy-<oligo (3-(R)-hydroxybutyric acid-co-3-(R)-hydroxyvaleric acid) ethylene-oligo(3-(R)-hydroxybutyric acid-co-3-(R)-hydroxyvaleric acid) >-alt-(2,2,4-trimethylhexamethylene-1,6-diisocyanate))-co-(α,ω-dihydroxy-<oligo(ε-caprolactone)-ethylenoxyethylene-oligo-(ε-caprolactone)>-alt-(2,2,4-trimethylhexamethylene-1,6-diisocyanate))) (Formula 10 on the sheet of formulas)

24.58 g (10.73 mmol) of PHB/HV-diol and 24.58 g (20.42 mmol) of PCL-diol were dissolved in 100 ml of 1,2-dichloroethane in a two-necked flask at 80° C. The solvent was then distilled off at an oil bath temperature of 110° C. until a slightly viscous, still stirrable solution remained in the flask and the water content of the last 10 ml of the distillate was 40 ppm. A stream of nitrogen was then passed over the apparatus. After the temperature of the oil bath had been reduced to 80° C., 6.5427 g (31.16 mmol) of 2,2,4-trimethylhexamethylene diisocyanate were added. To keep the stirrer moving, the mixture can be diluted with 1,2-dichloroethane. After a reaction time of 162.5, 186.5 and 216 hours, 46, 16 and 16 mg respectively (M=631.56 g/mol) of dibutyltin dilaurate were added from a 0.073M stock solution in 1,2-dichloroethane. After 283 hours, the reaction was stopped by precipitation of the polymer solution in low boiling petroleum ether.

Purification:

The polymer was dissolved again in 1,2-dichloroethane and precipitated as a solution in low-boiling petroleum ether. Thereafter, the polymer was dissolved again in dioxane and filtered through a G4 auction filter, before the polymer from the dioxane solution was precipitated in slightly basic deionized water. The pH of the water was brought to 8–9 with sodium bicarbonate. Thereafter, the polymer was precipitated a second time from a dioxane solution in deionized water.

Example 11—Preparation of poly(α,ω-dihydroxy-<oligo(3-(R)-hydroxybutyric acid-co-3-(R)-hydroxyvaleric acid) ethylene-oligo(3-(R)-hydroxybutyric acid-co-3-(R)-hydroxyvaleric acid) >-alt-(2,6-diisocyanatocaproic acid methylester))-co-(α,ω-dihydroxy-<oligo(ε-caprolactone)>-ethylenoxyethylene-oligo-(ε-caprolactone)>-alt-(2,6-diisocyanatocaproic acid methyl ester)() (Formula 11 on the sheet of formulas)

18.00 g (7.86 mmol) of PHB/HV-diol and 18.00 g (14.95 mmol) of PCL-diol were dissolved in 100 ml of 1,2-dichloroethane in a two-necked flask at 80° C. 20 ml of the solvent were then distilled off at an oil bath temperature of 110° C. Thereafter, the solvent was distilled over a Soxhlet apparatus filled with about 30 g of A4 molecular sieves (4 Å pore size) until the water content in the Soxhlet apparatus was 3.8 ppm. The solution was concentrated by distilling off solvent until a slightly viscous, still stirrable solution remained in the flask. The apparatus was then placed under a slight increased pressure of nitrogen. After the temperature of the oil bath had been reduced to 80° C., 4.845 g (22.83 mmol) of lysine methyl ester diisocyanate were added. To keep the stirrer moving, a little dry 1,2-dichloroethane can be added as required. After a reaction time of 188.75 hours, 0.138 g (0.65 mmol) of lysine methyl ester diisocyanate were added. After 194.25 hours, the reaction was stopped by precipitation of the polymer solution in low-boiling petroleum ether.

Purification:

The polymer was dissolved in dioxane and the solution was filtered through a G4 suction filter, before the polymer was precipitated from the dioxane solution in deionized water. Thereafter, the polymer was precipitated again from a dioxane solution in deionized water.

Example 12—Preparation of poly((α,ω-dihydroxy-<oligo (3-(R)-hydroxybutyric acid-co-3-(R)-hydroxyvaleric acid) ethylene-oligo(3-(R)-hydroxybutyric acid-co-3-(R)-hydroxyvaleric acid) >-alt-(2,6-diisocyanatocaproic acid methyl ester))-co-(α,ω-dihydroxy-<oligo(adipic acid-alt-(butanediol; diethylene glycol; ethylene glycol))>alt-(2,6-diisocyanatocaproic acid methyl ester))) Formula 12 on the sheet of formulas)

10.02 g (4.38 mmol) of PHB/HV-diol and 10.02 (10.02 mmol) of DIOREZ were dissolved in 100 ml of 1,2-dichloroethane in a two-necked flask at 80° C. 20 ml of the solvent were then distilled off at an oil bath temperature of 110° C. Thereafter, the solvent was distilled over a Soxhlet apparatus; filled with about 30 g of A4 molecular sieves (4 Å pore size) until the water content in the Soxhlet apparatus was 4.5 ppm. The solution was concentrated by distilling off solvent until a slightly viscous, still stirrable solution remained in the flask. The apparatus was then placed under a slight increased pressure of nitrogen. After the temperature of the oil bath had been reduced to 80° C., 3.0818 g (14.52 mmol) of lysine methyl ester diisocyanate were added. To keep the stirrer moving, a little dry 1,2-dichloroethane can be added as required. After a reaction time of 76.2 hours, 0.08 g (0.38 mmol) of lysine methyl ester diisocyanate were added. After 166.3 hours, the reaction was stopped by precipitation of the polymer solution in low-boiling petroleum ether.

Purification:

The polymer was dissolved in dioxane and the solution was filtered through a G4 suction filter, before the polymer was precipitated from the dioxane solution in deionized water. Thereafter, the polymer was precipitated again from a dioxane solution in deionized water.

Example 13—Preparation of poly(($\alpha,\omega$-dihydroxy-oligo(3-(R)-hydroxybutyric acid-co-3-(R)-hydroxyvaleric acid) ethylene-oligo(3-(R)-hydroxybutyric acid-co-3-(R)-hydroxyvaleric acid))-alt-sebacic acid)-co-($\alpha,\omega$-dihydroxy-(oligo(adipic acid-alt-(butanediol; diethylene glycol; ethylene glycol)))-alt-sebacic acid)) (Formula 13 on the sheet of formulas)

10.00 g ($1.00 \times 10^{-2}$ mol) of DIOREZ-diol and 10.00 g ($4.35 \times 10^{-3}$ mol) of PHB-diol were added to 150 ml of dichloroethane. The reaction mixture was dried to a water content of 5 ppm by means of azeotropic distillation over a Soxhlet apparatus filled with molecular sieves (5 Å) under a nitrogen atmosphere for 5 hours. The reaction solution was then cooled to an ice bath temperature. Thereafter, 2.38 g ($3.01 \times 10^{-2}$ mol, 105%, <15 ppm of $H_2O$) of pyridine and catalyst (dimethylaminopyridine, 0.1% by weight) were added. 3.43 g ($1.44 \times 10^{-2}$ mol) of sebacic acid dichloride were then added to the clear solution. The reaction was carried out at 4° C. until the molecular weight reached its maximum. The reaction mixture was dissolved in dichloroethane and the solution was poured into a vessel filled with 10 liters of distilled water. The aqueous solution was changed at regular intervals of time. The polymer was then freed from the water and from the solvent and dried at 50° C., 200 mbar for 12 hours. It was then dissolved again in dioxane, precipitated in water, filtered off and dried at 50° C. in a high vacuum.

Example 14—Preparation of poly(($\alpha,\omega$-dihydroxy-<oligo(3-(R)-hydroxybutyric acid-co-3-(R)-hydroxyvaleric acid) ethylene-oligo(3-(R)-hydroxybutyric acid-co-3-(R)-hydroxyvaleric acid))-alt-sebacic acid)-co-($\alpha,\omega$-dihydroxy-(oligo($\epsilon$-caprolactone)-ethylenoxyethylene-oligo($\epsilon$-caprolactone))-alt-sebacic acid)) (Formula 14 on the sheet of formulas)

10.00 g ($8.33 \times 10^{-3}$ mol) of PCL-diol and 10.00 g ($4.35 \times 10^{-3}$ mol) of PHB-diol were added to 150 ml of dichloroethane. The reaction mixture was dried to a water content of 5 ppm by means of azeotropic distillation over a Soxhlet apparatus filled with molecular sieves (5 Å) under a nitrogen atmosphere for 5 hours. The reaction solution was then cooled to an ice bath temperature. Thereafter, 2.11 g ($2.66 \times 10^{-2}$ mol, 105%, <15 ppm of $H_2O$) of pyridine and catalyst (dimethylaminopyridine, 0.1% by weight) were added. 3.03 g ($1.27 \times 10^{-2}$ mol) of sebacic acid dichloride were then added to the clear solution. The reaction was carried out at 4° C. until the molecular weight reached its maximum.

The reaction mixture was dissolved in dichloroethane and the solution was poured into a vessel filled with 10 liters of distilled water. The aqueous solution was changed at regular intervals of time. The polymer was then freed from the water and from the solvent and dried at 50° C., 200 mbar for 12 hours. It was then dissolved again in dioxane, precipitated in water, filtered off and dried at 50° C. in a high vacuum.

Example 15—Preparation of poly(($\alpha,\omega$-dihydroxy-(oligo(3-(R)-hydroxybutyric acid-co-3-(R)-hydroxyvaleric acid) ethylene-oligo(3-(R)-hydroxybutyric acid-co-3-(R)-hydroxyvaleric acid))-alt-sebacic acid)-co-($\alpha,\omega$-dihydroxy-(oligo(tetra-methylenoxy))-alt-sebacic acid)) (Formula 15 on the sheet of formulas)

10.00 g ($1.54 \times 10^{-2}$ mol) of PHB-diol and 10.00 g ($4.35 \times 10^{-3}$ mol) of PHB-diol were added to 150 ml of dichloroethane. The reaction mixture was dried to a water content of 5 ppm by means of azeotropic distillation over a Soxhlet apparatus filled with molecular sieve (5 Å) under a nitrogen atmosphere for 5 hours. The reaction solution was then cooled to an ice bath temperature. Thereafter, 3.28 g ($4.15 \times 10^{-2}$ mol, 105%, <15 ppm of $H_2O$) of pyridine and catalyst (dimethylaminopyridine, 0.1% by weight) were added. 4.72 g ($1.97 \times 10^{-2}$ mol) of sebacic acid dichloride were then added to the clear solution. The reaction was carried out at 4° C. until the molecular weight reached its maximum.

The reaction mixture was dissolved in dichloroethane and the solution was poured into a vessel filled with 10 liters of distilled water. The aqueous solution was changed at regular intervals of time. The polymer was then freed from the water and from the solvent and dried at 50° C., 200 mbar for 12 hours. It was then dissolved again in dioxane, precipitated in water, filtered off and dried at 50° C. in a high vacuum.

Semimicrobatch (Examples 16–20)

Example 16—Preparation of poly(poly($\alpha,\omega$-dihydroxy-poly(3-(R)-hydroxybutyrate)-ethylene-poly(3-(R)-hydroxybutyrate-alt-2,2,4-trimethylhexamethylene-1,6-diisocyanate)-co-poly($\alpha,\omega$-dihydroxy-(oligo(glycolide-ran-$\epsilon$-caprolactone)-ethylene-oligo(glycolide-ran-$\epsilon$-caprolactone))-alt-2,2,4-trimethylhexamethylene-1,6-diisocyanate)) The polymer contains the segments PHB and SG3000.

2.500 g (1.1 mmol) of PHB-diol ($\alpha,\omega$-dihydroxy-poly(3-(R)-hydroxybutyrate)-ethylene-poly(3-(R)-hydroxybutyrate))) and 2.500 g (1.0 mmol) of SG3000 ($\alpha,\omega$-dihydroxy-(oligo(glycolide-ran-$\epsilon$-caprolactone)-ethylene-oligo(glycolide-ran-$\epsilon$-caprolactone)) were dissolved in 70 ml of dry (water content <5 ppm, determined by the Karl Fischer method) 1,2-dichloroethane at 70° C. This procedure was carried out in a standard reflux apparatus under $N_2$. To dry the reaction mixture, the water-containing azeotrope of the solvent was distilled in a Soxhlet extractor over 4 Å molecular sieves. The bath temperature was 110° C. The molecular sieves were changed as often as necessary until a water content of <5 ppm was reached in the solvent distilled off. Solvent was then distilled off until a slightly viscous, still stirrable solution remained in the flask. After the bath temperature had fallen to 80° C., 0.441 g (2.1 mmol) of 2,2,4-trimethylhexamethylene diisocyanate was added. To keep the stirrer moving, a little dry 1,2-dichloroethane can be added if required. The reaction was stopped after 284 hours by precipitation in a hexane fraction.

Purification:

The polymer was dissolved again in dry 1,2-dichloroethane and precipitated as a solution in a hexane fraction.

The results of degradation experiments on the block copolymers of Examples 9 to 16 are summarized in Table 1.

TABLE 1

|  | | | Hydrolytic degradation in vitro | | | Degradation in vivo* | |
|---|---|---|---|---|---|---|---|
| Example | $M_w$*** | pH | Duration (Days) | T (°C.) | **Decrease in $M_w$ to % of the original value | Duration (Days) | **Decrease in $M_w$ to % of original value |
| 9 | 75000 | 7.0 | 270 | 37 | 45.3 | 270 | 70.8 |
| 10 | 75000 | 7.0 | 270 | 37 | 62.7 | 270 | 50.7 |
| 11 | 77000 | 7.0 | 165 | 37 | 72.7 | 165 | 80.5 |
| 13 | 49800 | 7.2 | 104 | 37 | 56.2 | | |
| 14 | 44000 | 7.4 | 104 | 37 | 26.1 | | |
| 16 | 73300 | 7.0 | 13 | 70 | 6.8 | | |

*Implanted subcutaneously as a film
**Measured on recovered material
***$M_w$ starting material (film)

Example 17—Preparation of poly(poly(α,ω-dihydroxy-poly(3-(R)-hydroxybutyrate)-ethylene-poly(3-(R)-hydroxybutyrate-alt-2,2,4-trimethylhexamethylene-1,6-diisocyanate)-co-poly(α,ω-dihydroxy-(oligo(glycolide-block-ε-caprolactone)-ethylene-oligo(glycolide-block-ε-caprolactone))-alt-2,2,4-trimethylhexamethylene-1,6-diisocyanate)) The polymer contains the segments PHB and HG3000.

2.500 g (1.1 mmol) of PHB-diol (α,ω-dihydroxy-(poly(3(R)-hydroxybutyrate)-ethylene-poly(3-(R)-hydroxybutyrate))) and 2.500 g (1.0 mmol) of HG3000 (α,ω-dihydroxy-(oligo(glycolide-block-ε-caprolactone)-ethylene-oligo(glycolide-block-ε-caprolactone)) were dissolved in 15 ml of dry dimethylacetamide (water content <5 ppm, determined by the Karl Fischer method) and 70 ml of dry (water content <5 ppm, determined by the Karl Fischer method) 1,2-dichloroethane at 70° C. This procedure was carried out in a standard reflux apparatus under $N_2$. To dry the reaction mixture, the water-containing azeotrope of the solvent was distilled in a Soxhlet extractor over 4 Å molecular sieves. The bath temperature was 110° C. The molecular sieves were changed as often as necessary until a water content of <5 ppm was reached in the solvent distilled off. 1,2-Dichloroethane was now distilled off until a slightly viscous, still stirrable solution remained in the flask. After the bath temperature had fallen to 80° C. 0.441 g (2 1 mol) of 2,2,4-trimethylhexamethylene diisocyanate was added. To keep the stirrer moving, a little dry dimethylacetamide can be added if required. The reaction was stopped after 330 hours by precipitation in a hexane fraction.
Purification:

The polymer was dissolved again in dry dimethylacetamide and precipitated as a solution in a hexane fraction.

Example 18—Preparation of poly(poly(α,ω-dihydroxy-poly(3-(R)-hydroxybutyrate)-ethylene-poly(3-(R)-hydroxybutyrate-alt-2,2,4-trimethylhexamethylene-1,6-diisocyanate)-co-poly(α,ω-dihydroxy-(oligo(glycolide-block-ε-caprolactone)-ethylene-oligo(glycolide-block-ε-caprolactone))-alt-2,2,4-trimethylhexamethylene-1,6-diisocyanate)) The polymer contains the segments PHB and SG500.

2.500 g (1.1 mmol) of PHB-diol (α,ω-dihydroxy-poly(3-(R)-hydroxybutyrate)-ethylene-poly(3-(R)-hydroxybutyrate))) and 2.500 g (5.3 mmol) of SG500 (α,ω-dihydroxy-(oligo(glycolide-block-ε-caprolactone)-ethylene-oligo(glycolide-block-ε-caprolactone)) were dissolved in 15 ml of dry dimethylacetamide (water content <5 ppm, determined by the Karl Fischer method) and 70 ml of dry (water content <5 ppm, determined by the Karl Fischer method) 1,2-dichloroethane at 70° C. This procedure was carried out in a standard reflux apparatus under $N_2$. To dry the reaction mixture, the water-containing azeotrope of the solvent was distilled in a Soxhlet extractor over 4 Å molecular sieves. The bath temperature was 110° C. The molecular sieves were changed as often as necessary until a water content of <5 ppm was reached in the solvent distilled off. Solvent was now distilled off until a slightly viscous, still stirrable solution remained in the flask. After the bath temperature had fallen to 80° C., 1.335 g (6.4 mmol) of 2,2,4-trimethylhexamethylene diisocyanate were added. To keep the stirrer moving, a little dry dimethylacetamide can be added if required. The reaction was stopped after 330 hours by precipitation in a hexane fraction.
Purification:

The polymer was dissolved again in dry 1,2-dichloroethane and precipitated as a solution in a hexane fraction.

Example 19—Preparation of poly(poly(α,ω-dihydroxy-oligo(glycolide-block-ε-caprolactone)-ethylene-oligo(glycolide-block-ε-caprolactone))-alt-2,2,4-trimethylhexamethylene-1,6-diisocyanate)-co-poly(α,ω-dihydroxy-(oligo(glycolide-ran-ε-caprolactone)-ethylene-oligo(glycolide-ran-ε-caprolactone))-alt-2,2,4-trimethylhexamethylene-1,6-diisocyanate) The polymer contains the segments HG3000 and SG3000.

Preparation of a stock solution: 1.000 g (0.4 mmol) of HG3000 (α,ω-dihydroxy-(oligo(glycolide-block-ε-caprolactone))-ethylene-oligo(glycolide-block-ε-caprolactone) and 1.000 g (0.4 mmol) of SG3000 (α,ω-dihydroxy-(oligo(glycolide-ran-ε-caprolactone)) were dissolved in 20.000 g of dry diglyme (water content <10 ppm, determined by the Karl Fischer method). For drying, the solution was left to stand over 4 Å molecular sieves. The molecular sieves were replaced after 24 hours. This operation was repeated 2 to 3 times.

Polymerization: 11.000 g of stock solution were introduced into a two-necked flask which was a constituent of a standard reflux apparatus. After a bath temperature of 75° C. had been reached, 0.0841 g (0.4 mol) of 2,2,4trimethylhexamethylene diisocyanate was added. To keep the stirrer moving, a little dry diglyme can be added if required. The reaction was stopped after 230 hours by precipitation in a hexane fraction.
Purification:

The polymer was dissolved again in dry diglyme and precipitated as a solution in a hexane fraction.

Example 20—Preparation of poly(poly(α,ω-dihydroxy-oligo(glycolide-block-ε-caprolactone)-ethylene-oligo (glycolide-block-ε-caprolactone))-alt-2,2,4-trimethylhexamethylene-1,6-diisocyanate)-co-poly(α,ω-dihydroxy-(oligo(glycolide-block-ε-caprolactone)-ethylene-oligo(glycolide-block-ε-caprolactone))-alt-2,2,4-trimethylhexamethylene-1,6-diisocyanate)) The polymer contains the segments HG3000-SG500.

Preparation of a stock solution: 1.000 g (0.4 mmol) of HG3000 (α,ω-dihydroxy-(oligo(glycolide-block-ε-caprolactone)-ethylene-oligo(glycolide-block-ε-caprolactone) and 1.000 g (2.1 mmol) of SG500 (α,ω-dihydroxy-(oligo(glycolide-block-ε-caprolactone))-ethylene-oligo(glycolide-block-ε-caprolactone)) were dissolved in 20,000 g of dry diglyme (water content: <10 ppm, determined by the Karl Fischer method). For drying, the solution was left to stand over 4 Å molecular sieves. The molecular sieves were replaced after 24 hours. This operation was repeated 2 to 3 times.

Polymerization: 11.000 g of stock solution were introduced into a two-necked flask which was a constituent of a standard reflux apparatus. After a bath temperature of 75° C. had been reached, 0.2629 g (1.3 mmol) of 2,2,4trimethylhexamethylene diisocyanate was added. To keep the stirrer moving, a little dry diglyme can be added if required. The reaction was stopped after 230 hours by precipitation in a hexane fraction.
Purification:

The polymer was dissolved again in dry diglyme and precipitated as a solution in a hexane fraction.
Macrobatch—(Examples 21–27)

Example 21—Preparation of poly(poly(α,ω-dihydroxy-poly(3-(R)-hydroxybutyrate)-ethylene-poly(3-(R)-hydroxybutyrate-alt-2,2,4-trimethylhexamethylene-1,6-diisocyanate)-co-poly(α,ω-dihydroxy-(oligo(glycolide-ran-ε-caprolactone)-ethylene-oligo(glycolide-ran-ε-caprolactone))-alt-2,2,4-trimethylhexamethylene-1,6-diisocyanate)) The polymer contains the segments PHB and SG3000.

20.000 g (8.7 mmol) of PHB-diol (α,ω-dihydroxy-poly(3-(R)-hydroxybutyrate)-ethylene-poly(3-(R)-hydroxybutyrate))) and 20.000 g (8.1 mmol) of SG3000 α,ω-dihydroxy-(oligo(glycolide-ran-ε-caprolactone)-ethylene-oligo(glycolide-ran-ε-caprolactone))were dissolved in 250 ml of dry (water content <5 ppm, determined by the Karl Fischer method) 1,2-dichloroethane at 70° C. This procedure was carried out in a standard reflux apparatus under $N_2$. To dry the reaction mixture, the water-containing azeotrope of the solvent was distilled in a Soxhlet extractor over 4 Å molecular sieves. The bath temperature was 110° C. The molecular sieves were changed as often as necessary until a water content of <5 ppm was reached in the solvent distilled off. Solvent was now distilled off until a slightly viscous, still stirrable solution remained in the flask. After the bath temperature had fallen to 80° C., 3.5250 g (16.8 mmol) of 2,2,4-trimethylhexamethylene diisocyanate were added. To keep the stirrer moving, a little dry 1,2-dichloroethane can be added if required. The reaction was stopped after 280 hours by precipitation in a hexane fraction.
Purification:

The polymer was dissolved again in dry 1,2-dichloroethane and precipitated as a solution in a hexane fraction.

Example 22—Preparation of poly(poly(α,ω-dihydroxy-poly(3-(R)-hydroxybutyrate)-ethylene-poly(3-(R)-hydroxybutyrate-alt-2,2,4-trimethylhexamethylene-1,6-diisocyanate)-co-poly(α,ω-dihydroxy-(oligo(glycolide-block-ε-caprolactone)-ethylene-oligo(glycolide-block-ε-caprolactone))-alt-2,2,4-trimethylhexamethylene-1,6-diisocyanate)) The polymer contains the segments PHB and HG3000. (Formula 22 on the sheet of formulas)

20.000 g (8.7 mmol) of PHB-diol (α,ω-dihydroxy-poly(3-(R)-hydroxybutyrate)-ethylene-poly(3-(R)-hydroxybutyrate))) and 20.000 g (8.1 mmol) of HG3000 (α,ω-dihydroxy-(oligo(glycolide-block-ε-caprolactone)-ethylene-oligo(glycolide-block-ε-caprolactone)) were dissolved in 60 ml of dry dimethylacetamide (water content <5 ppm, determined by the Karl Fischer method) and 250 ml of dry (water content <5 ppm, determined by the Karl Fischer method) 1,2-dichloroethane at 70° C. This procedure was carried out in a standard reflux apparatus under $N_2$. To dry the reaction mixture, the water-containing azeotrope of the solvent was distilled in a Soxhlet extractor over 4 Å molecular sieves. The bath temperature was 110° C. The molecular sieves were changed an often as necessary until a water content of <5 ppm was reached in the solvent distilled off. 1,2-Dichloroethane was now distilled off until a slightly viscous, still stirrable solution remained in the flask. After the bath temperature had fallen to 80° C., 3.5327 g (16.8 mmol) of 2,2,4-trimethylhexamethylene diisocyanate were added. To keep the stirrer moving, a little dry dimethylacetamide can be added if required. The reaction was stopped after 330 hours by precipitation in a hexane fraction.
Purification:

The polymer was dissolved again in dry 1,2-dimethylacetamide and precipitated as a solution in a hexane fraction.

Example 23—Preparation of poly(poly(α,ω-dihydroxy-poly(3(R)-hydroxybutyrate)-ethylene-poly(3-(R)-hydroxybutyrate))-alt-2,2,4-trimethylhexamethylene-1,6-diisocyanate)-co-poly(α,ω-dihydroxy-(oligo(glycolide-block-ε-caprolactone)-ethylene-oligo(glycolide-block-ε-caprolactone))-alt-2,2,4-trimethylhexamethylene-1,6-diisocyanate)) The polymer contains the segments PHB and SG500. (Formula 23 on the sheet of formulas)

20.000 g (8.7 mmol) of PHB-diol (α,ω-dihydroxy-poly(3-(R)-hydroxybutyrate)-ethylene-poly(3-(R)-hydroxybutyrate))) and 20.000 g (42.1 mmol) of SG500 (α,ω-dihydroxy-(oligo(glycolide-block-ε-caprolactone) ethylene-oligo(glycolide-block-ε-caprolactone)) were dissolved in 60 ml of dry dimethylacetamide (water content <5 ppm, determined by the Karl Fischer method) and 250 ml of dry (water content <5 ppm, determined by the Karl Fischer method) 1,2-dichloroethane at 70° C. This procedure was carried out in a standard reflux apparatus under $N_2$. To dry the reaction mixture, the water-containing azeotrope of the solvent was distilled in a Soxhlet extractor over 4 Å molecular sieves. The bath temperature was 110° C. The molecular sieves were changed as often as necessary until a water content of <5 ppm was reached in the solvent distilled off. 1,2-Dichloroethane was now distilled off until a slightly viscous, still stirrable solution remained in the flask. After the bath temperature had fallen to 80° C., 10.68 g (50.8 mmol) of 2,2,4-trimethylhexamethylene diisocyanate was added. To keep the stirrer moving, a little dry dimethylacetamide can be added if required. The reaction was stopped after 330 hours by precipitation in a hexane fraction.
Purification:

The polymer was dissolved again in dry dimethylacetamide and precipitated as a solution in a hexane fraction.

Example 24—Preparation of poly(poly(α,ω-dihydroxy-(oligo-(glycolide-block-ε-caprolactone)-ethylene-oligo(glycolide-block-ε-caprolactone))-alt-2,2,4-trimethylhexamethylene-1,6-diisocyanate)-co-poly(α,ω-dihydroxy-(oligo(glycolide-ran-ε-caprolactone)-ethylene-oligo(glycolide-ran-ε-caprolactone))-alt-2,2,4- trimethylhexamethylene-1,6-diisocynate)) The polymer contains the segments HG3000 and SG3000.

Preparation of a stock solution: 10.000 g (40 mmol) of HG3000 (α,ω-dihydroxy-(oligo(glycolide-block-ε-caprolactone)-ethylene-oligo(glycolide-block-ε-caprolactone)) and 10.000 g (4.0 mmol) of SG3000 (α,ω-dihydroxy-(oligo(glycolide-ran-ε-caprolactone)-ethylene-oligo(glycolide-ran-ε-caprolactone)) were dissolved in 20.000 g of dry diglyme (water content <10 ppm, determined by the Karl Fischer method). For drying, the solution was left to stand over 4 Å molecular sieves. The molecular sieves were replaced after 24 hours. This operation was repeated 2 to 3 times.

Polymerization: 110.000 g of stock solution were introduced into a two-necked flask which was a constituent of a standard reflux apparatus. After a bath temperature of 75° C. had been reached, 0.8495 g (4.0 nmol) of 2,2,4trimethylhexamethylene diisocyanate were added. To keep the stirrer moving, a little dry diglyme can be added if required. The reaction was stopped after 230 hours by precipitation in a hexane fraction.
Purification:

The polymer was dissolved again in dry diglyme and precipitated as a solution in a hexane fraction.

Example 25—Preparation of poly(poly(α,ω-dihydroxy-(oligo-(glycolide-block-ε-caprolactone)-ethylene-oligo-(glycolide-block-ε-caprolactone))-alt-2,2,4-trimethylhexamethylene-1,6-diisocyanate)-co-poly(α,ω,dihydroxy-(oligo(glycolide-block-ε-caprolactone)-ethylene-oligo(glycolide-block-ε-caprolactone))-alt-2,2,4-trimethylhexamethylene-1,6-diisocyanate)). The polymer contains the segments HG3000-SG500. (Formula 25 on the sheet of formulas)

Preparation of a stock solution: 10.000 g (4.0 mmol) of HG3000 (α,ω-dihydroxy-(oligo(glycolide-block-ε-caprolactone)-ethylene-oligo(glycolide-block-ε-caprolactone)) and 10,000 g (21.1 mmol) of SG500 (α,ω-dihydroxy-(oligo(glycolide-block-ε-caprolactone)-ethylene-oligo(glycolide-block-ε-caprolactone)) were dissolved in 20.000 g of dry diglyme (water content <10 ppm, determined by the Karl Fischer method). For drying, the solution was left to stand over 4 Å molecular sieves. The molecular sieves were replaced after 24 hours. This operation was repeated 2 to 3 times.

Polymerization: 110,000 g of stock solution were introduced into a two-necked flask which was a constituent of a standard reflux apparatus. After a bath temperature of 75° C. had been reached, 2.6340 g (12.5 mmol) of 2,2,4trimethylhexamethylene diisocyanate were added. To keep the stirrer moving, a little dry diglyme can be added if required. The reaction was stopped after 230 hours by precipitation in a hexane fraction.
Purification:

The polymer was dissolved again in dry diglyme and precipitated as a solution in a hexane fraction.

Example 26—Preparation of poly(poly(α,ω-dihydroxy-poly(3-(R)-hydroxybutyrate)-ethylene-poly(3-(R)-hydroxybutyrate))-alt-2,6-diisocyanatocaproic acid methyl ester)-co-poly(α,ω-dihydroxy-(oligo(ε-caprolactone))-ethylene-oligo(ε-caprolactone))-alt-2,6-diisocyanatocaproic acid methyl ester)-co-poly(phenazyl-10,11-dihydroxyundecanoate-alt-2,6-diisocyanatocaproic acid methyl ester)) (Formula 26 on the sheet of formulas)

2.0 g (0.833 mmol) of α,ω-dihydroxy-poly(3hydroxybutyrate) (PHB-diol) and 2.135 g (1.667 mmol) of polycaprolactonediol were dissolved in 100 ml of 1,2dichloroethane and the solution was dried to a water content of 4 ppm under reflux over a Soxhlet extractor filled with molecular sieves (4 Å-8/2). After concentration to a total of 10 ml, the solution was cooled to room temperature and the Soxhlet extractor was replaced by a reflux condenser with an inert gas attachment. 1.06 g (5.0 mmol) of L-lysine diisocyanate methyl ester (LIC) were added and the solution was stirred at 75° C. for about 24 hours. The course of the polymerization was monitored by gel permeation chromatography until no further increase in molecular weight took place. 0.84 g (2.5 mmol) of phenacyl-10,11-dihydroxyundecanoate was then added and the solution was stirred at 75° C. for a further 48 hours. A further 0.1 g (0.47 mmol) of LIC was then added and the reaction mixture was stirred at 75° C. until no further increase in molecular weight took place. The solution was cooled to room temperature and diluted to a total of 50 ml with 1,2-dichloroethane. The polymer was precipitated in petroleum ether (low-boiling fraction), filtered off and dried at 40° C. under 40 mbar in a drying cabinet for 24 hours.

Example 27—Preparation of poly(poly(α,ω-dihydroxy-poly(3(R)-hydroxybutyrate)-ethylene-poly(3-(R)-hydroxybutyrate))-alt-2,6-diisocyanatocaproic acid methyl ester)-co-poly(α,ω-dihydroxy-(oligo(ε-caprolactone)-ethylene-oligo(ε-caprolactone))-alt-2,6-diisocyanatocaproic acid methyl ester) -co-poly(10,11-dihydroxyundecanoic acid-alt-2,6-diisocyanatocaproic acid methyl ester))

0.9 g of the polymer described above were dissolved in 20 ml of acetic acid, and 6.9 g of zinc dust were added. The mixture was stirred at room temperature for 21 hours. The zinc was then filtered off and the polymer 2.6 precipitated in petroleum ether. According to NMR analysis, the phenacyl protective group of the phenacyl-10,11-dihydroxydecanoate unit was removed quantitatively, while the molecular weight of the polymer decreased by 8%.

Obviously numerous modifications and variations of the present invention are possible in light of the above teachings. It is, therefore, to be understood that within the scope of the appended claims, the invention may be practiced otherwise than as specifically described therein.

Formula 9

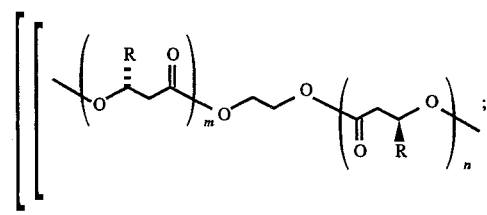

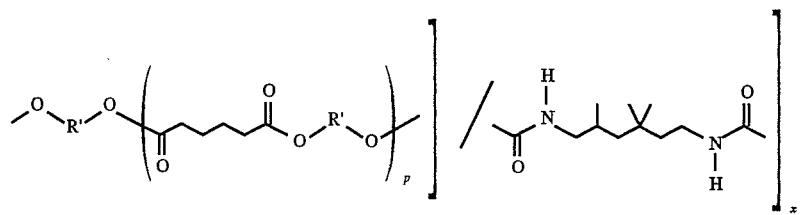
Formula 10
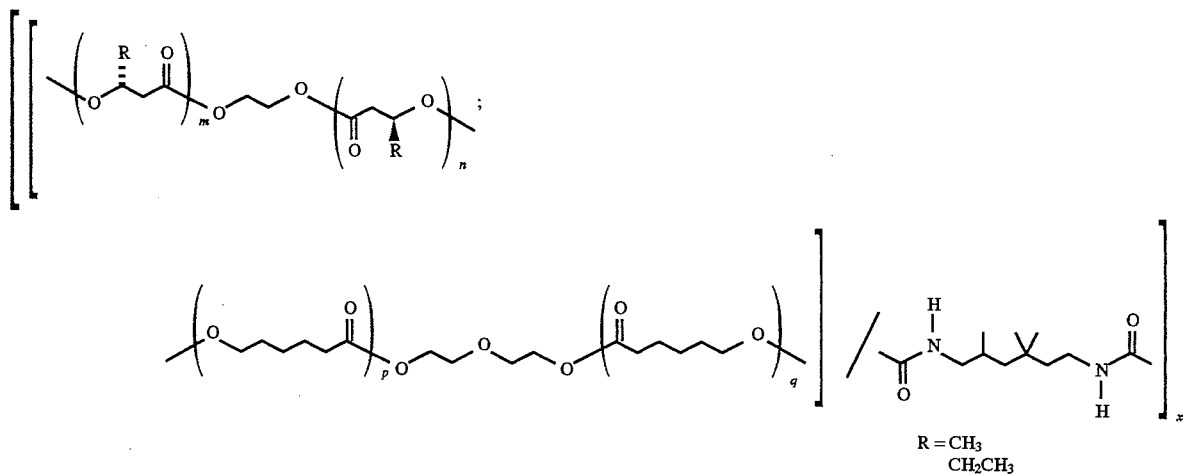
Formula 11
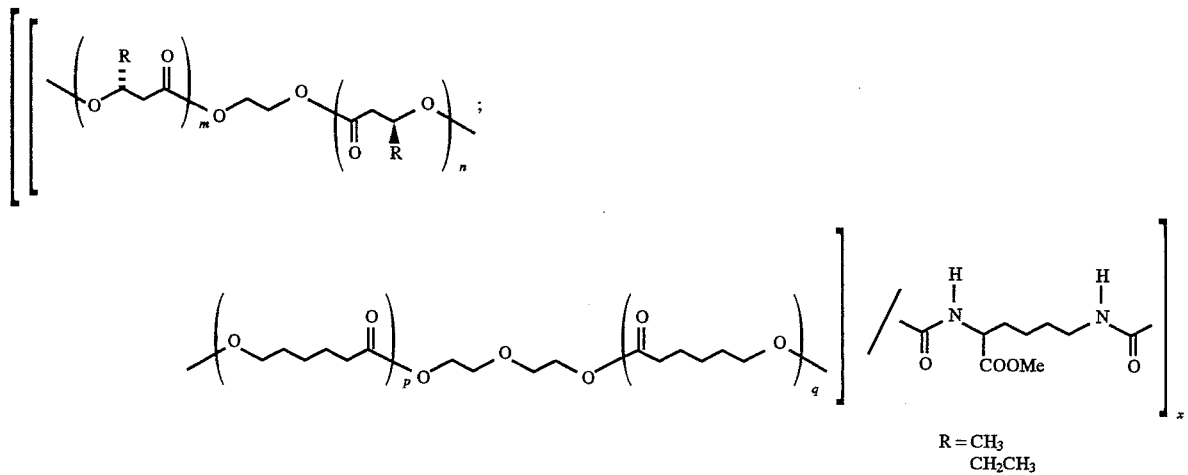
Formula 12
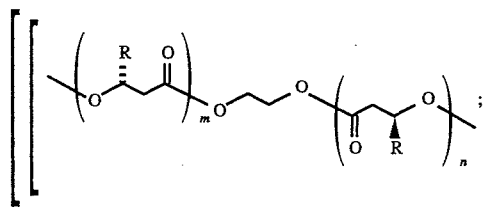

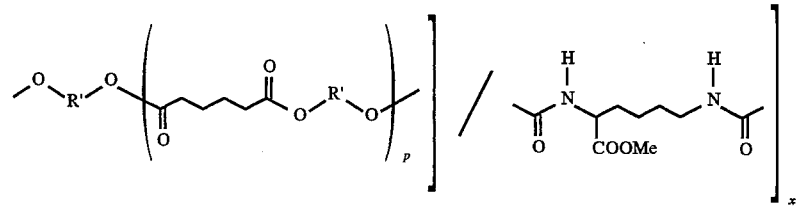
Formula 13
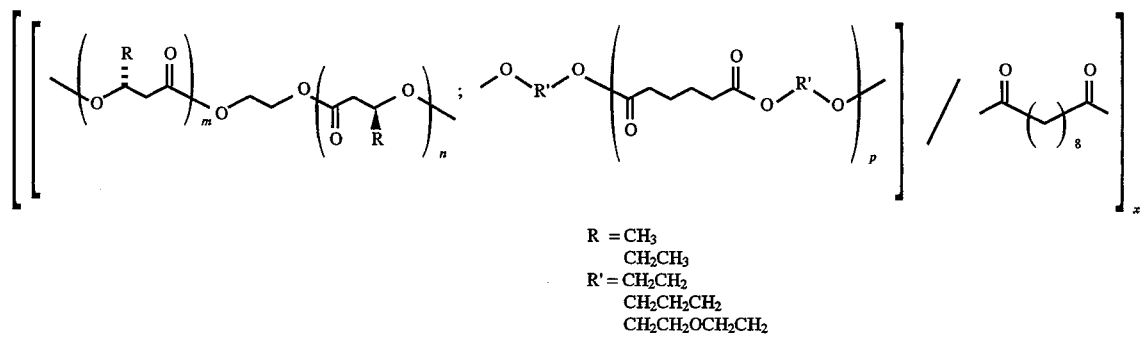
Formula 14
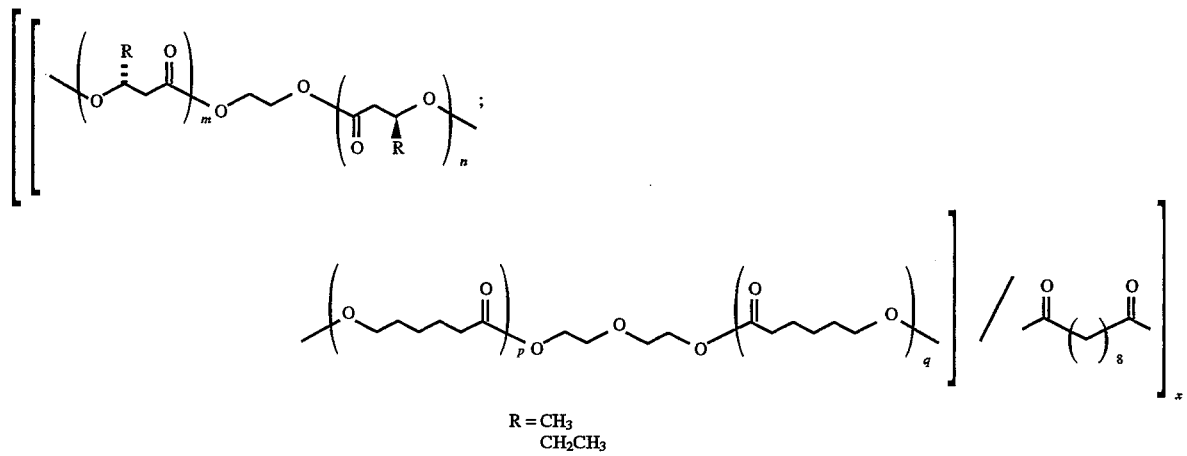
Formula 15
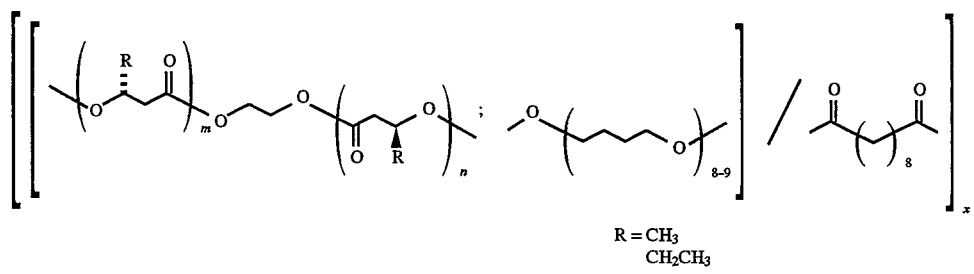
Formula 22
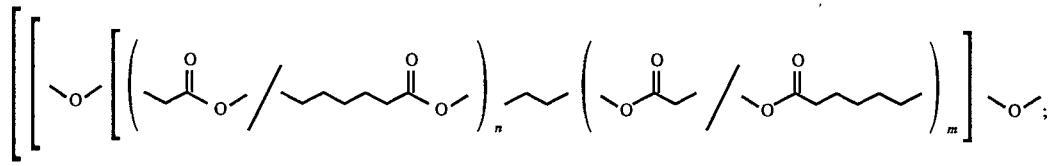

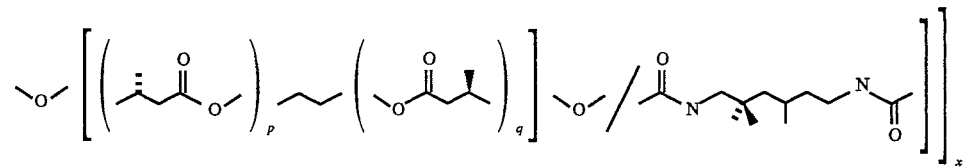
Formula 23
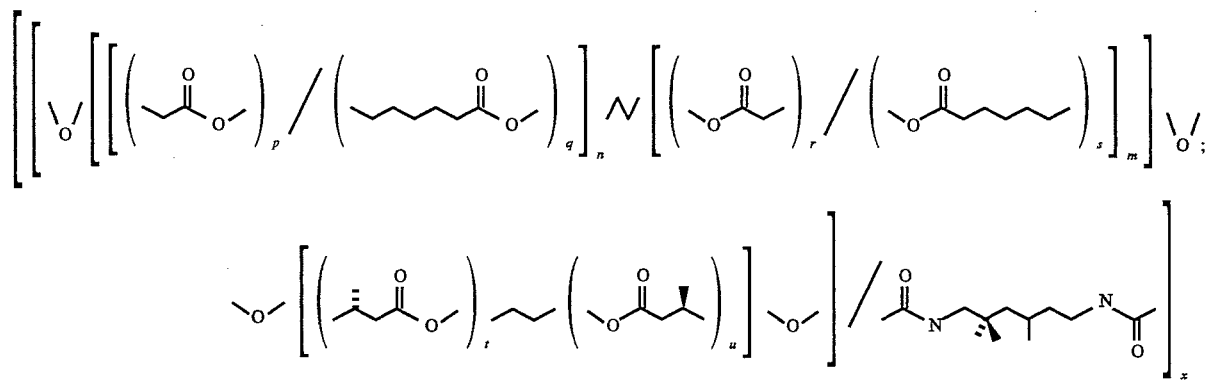
Formula 25
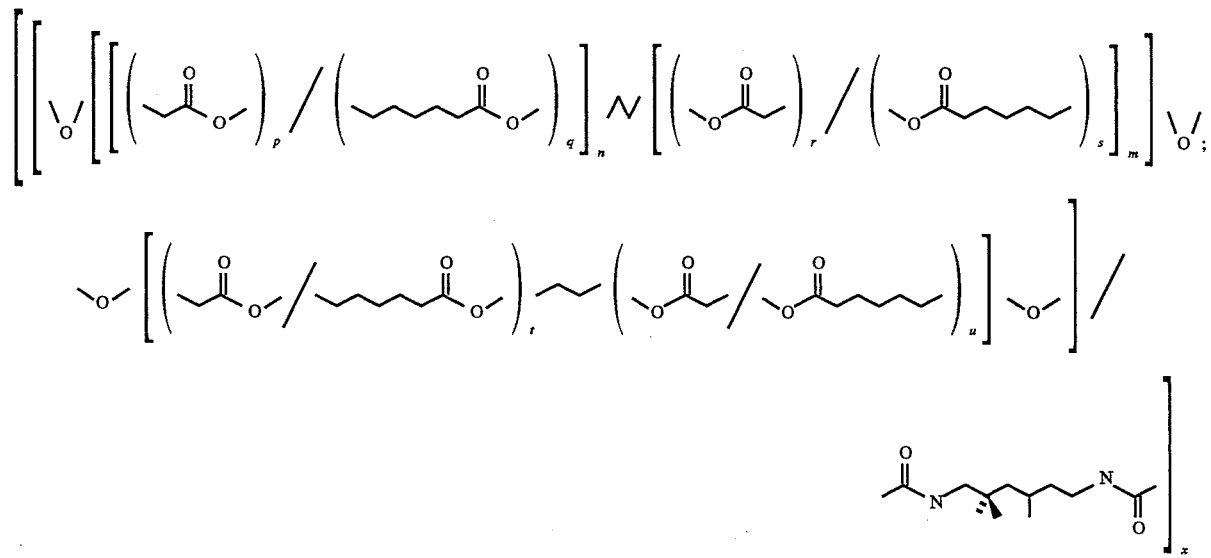
Formula 26
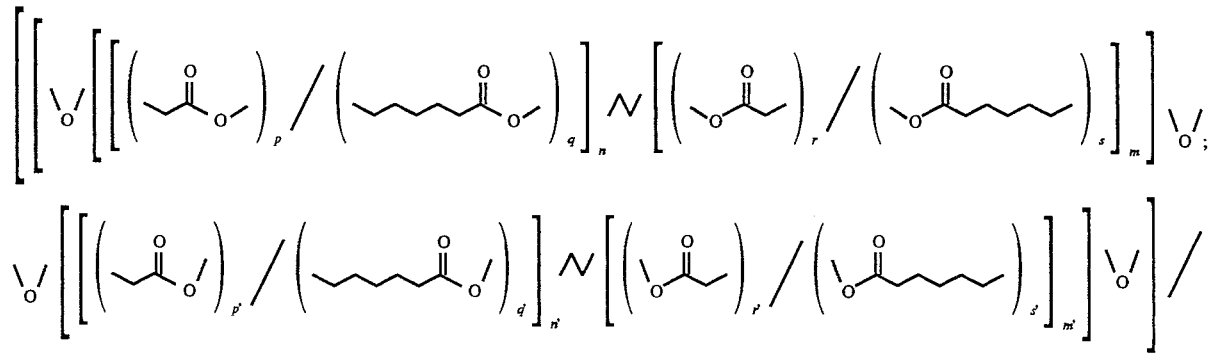

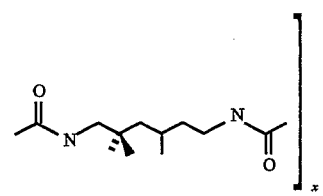

What is claimed as new and is desired to be secured by Letters Patent of the United States is:

1. A biocompatible multi-block copolymer, comprising at least two chemically different block units,
    (1) a first block obtained by transesterification of poly-(R)-3-hydroxybutyric acid or copolymers thereof with 3-hydroxyvaleric acid, with ethylene glycol, and
    (2) a second block comprising an α,ω-dihydroxypolyester which is different from said first block or an α,ω-dihydroxypolyether,
    wherein said multi-block copolymer is obtained by linear polycondensation of said first block and said second block with a diisocyanate, diacid halide or phosgene.

2. The block copolymer of claim 1, obtained by linear polycondensation with a diisocyanate.

3. The block copolymer of claim 1, obtained by linear polycondensation with an diacid halide.

4. The block copolymer of claim 1, obtained by linear polycondensation with phosgene.

5. The block copolymer of claim 1, wherein said α,ω-dihydroxypolyester is obtained by ring-opening polymerization of cyclic esters, lactones or mixtures thereof in the presence of an aliphatic diol, polyetherdiol or polyesterdiol.

6. The block copolymer of claim 5, wherein said cyclic esters or lactones are selected from the group consisting of (L,L)-dilactide, (D,D)-dilactide, (D,L)-dilactide, diglycolide, β-(R)-butyrolactone, β-(S)-butyrolactone, β-rac-butyrolactone, ε-caprolactone and mixtures thereof.

7. The block copolymer of claim 1, wherein said α,ω-dihydroxypolyether is α,ω-dihydroxypoly(oxyethylene-co-oxypropylene).

8. The block copolymer of claim 1, wherein said α,ω-dihydroxypolyester is α,ω-dihydroxypoly(adipic acid-alt-(ethylene glycol; diethylene glycol)), α,ω-dihydroxypoly(adipic acid-alt-(ethylene glycol; propylene glycol)), α,ω-dihydroxy-<oligo(ε-caprolactone)-ethylenoxyethylene-oligo-(ε-caprolactone), or polycaprolactone diol.

9. The block copolymer of claim 1, wherein at least one α,ω-dihydroxypolyester is a crystallizing compound which forms crystalline regions in the block copolymer at room temperature.

10. The block copolymer of claim 1, wherein at least one α,ω-dihydroxypolyester is a non-crystalline compound which forms amorphous regions in the block copolymer.

11. The block copolymer of claim 1, wherein at least one α,ω-dihydroxypolyester is a crystallizing or non-crystallizing compound which forms amorphous regions in the block polymer.

12. The block copolymer of claim 1, comprising crystalline and amorphous or several crystalline or several amorphous regions.

13. The block copolymer of claim 1, which is obtained by linear co-polycondensation of low molecular weight compounds having functional groups.

14. The block copolymer of claim 13, comprising chemically bonded pharmaceutically active compounds or diagnostic compounds.

15. The block copolymer of claim 1, wherein said block copolymer is biologically degradable.

16. The block copolymer of claim 15, which is degradable in a human or in an animal body.

17. The block copolymer of claim 1, which can be melt processed at a temperature of 80° C. to 200° C.

18. The block copolymer of claim 17, which can be melt processed at a temperature of 100° C. to 140° C.

19. A method of forming a medical implant using the block copolymer of claim 1.

20. The method of claim 19 wherein said medical implant is in the form of a tube with one or more channels.

21. The method of claim 19 wherein said medical implant has a porous structure.

22. The method of claim 21, wherein said medical implant forms a simple or composite biologically compatible tissue.

23. The method of claim 19, wherein said medical implant further comprises admixed particulate pharmaceutical active compounds or diagnostic compounds.

24. A method of forming a surgical aid intended for use in or on the body using the block copolymer of claim 1, wherein said surgical aid is formed at least partly of said block copolymer.

* * * * *